United States Patent [19]

Gilson

[11] Patent Number: 5,018,394
[45] Date of Patent: May 28, 1991

[54] CONTINUOUSLY ADJUSTABLE DILUTING DEVICE FOR MIXING PREDETERMINED VOLUMES OF LIQUID

[76] Inventor: Warren E. Gilson, 601 N. Segoe Rd., Unit #104, Madison, Wis. 53705

[21] Appl. No.: 463,283

[22] Filed: Jan. 10, 1990

[51] Int. Cl.⁵ .............................. G01N 1/14; B01L 3/02
[52] U.S. Cl. .................................................. 73/864.18
[58] Field of Search ................. 73/863, 864.18, 864.12, 73/864.11, 864.13–864.17; 436/179; 137/561 R

[56] References Cited

U.S. PATENT DOCUMENTS

| | | | |
|---|---|---|---|
| 3,184,122 | 5/1965 | Nerenberg | 73/864.12 X |
| 3,302,462 | 2/1967 | Pursell | 73/864.18 X |
| 3,334,788 | 8/1967 | Hamilton | 73/864.18 X |
| 3,492,876 | 2/1970 | Bull et al. | 73/864.18 X |
| 3,656,512 | 4/1972 | Countryman | 251/342 X |
| 4,128,009 | 12/1978 | D'Autry | 73/864.18 X |
| 4,141,250 | 2/1979 | D'Autry | 73/864.18 X |
| 4,369,665 | 1/1983 | Citrin | 73/864.18 |

FOREIGN PATENT DOCUMENTS 1439659  6/1976  United Kingdom ............. 73/864.18

*Primary Examiner*—Tom Noland
*Attorney, Agent, or Firm*—Mason, Kolehmainen, Rathburn & Wyss

[57] ABSTRACT

A continuously adjustable liquid mixing device for intermixing selectively adjustable volumes of several liquids comprises a body for holding a plurality of volumes of the liquids including a recess at an upper end. A mechanism is provided for drawing up the volumes of liquid into the body and thereafter expelling the same from a lower end. A volume adjusting selecting mechanism is provided for at least one of the volumes including a rotary element mounted in the recess and frictionally engaging a wall surface thereof for retaining a selected volume that is desired. A rotary drive system is provided for rotating the volume adjustment mechanism and is readily accessible externally of the body for convenient manipulation to select a desired volume. The drive system is movable between an outer operating position for easy manipulation and a retracted position when not in use.

18 Claims, 2 Drawing Sheets

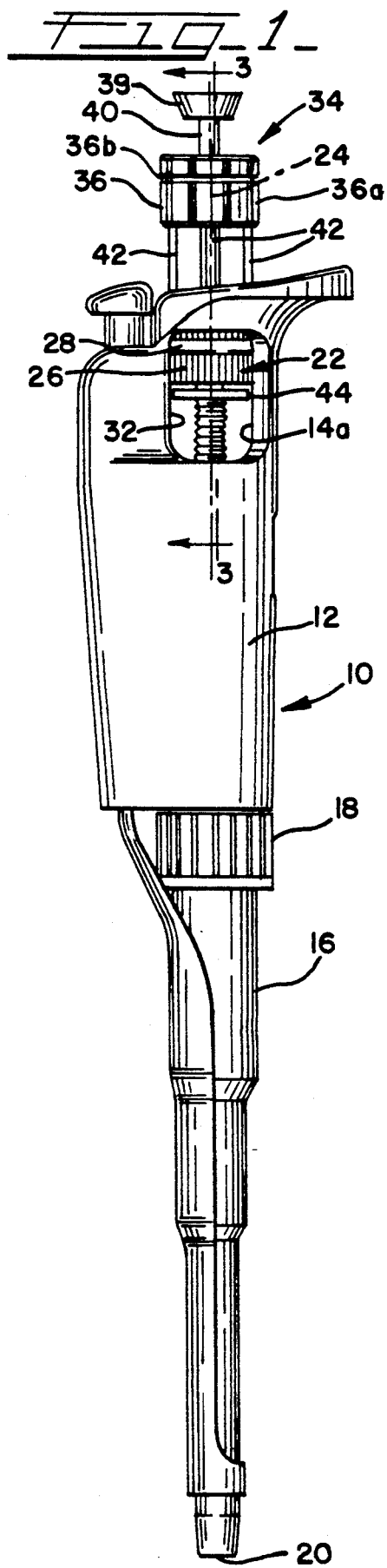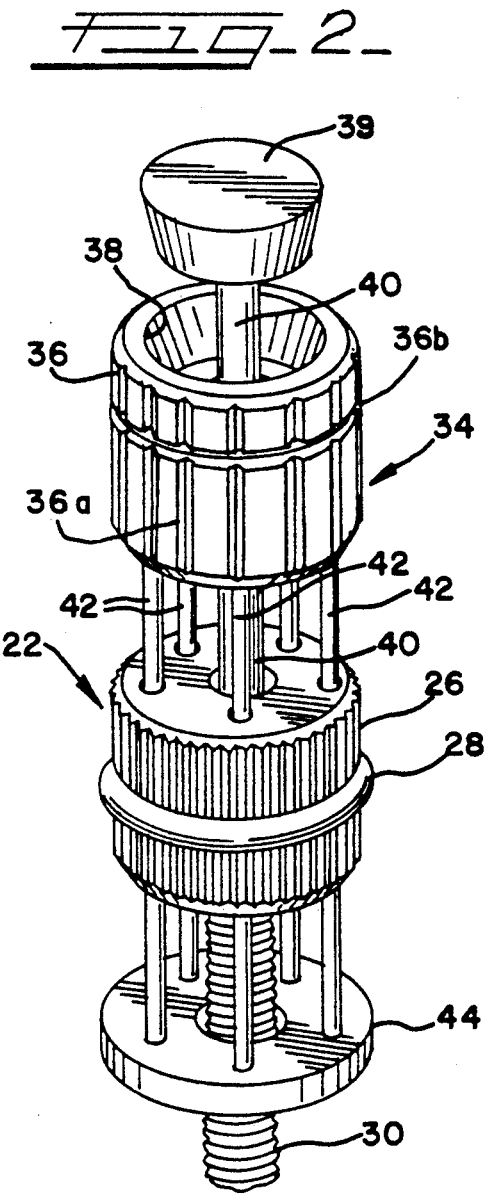

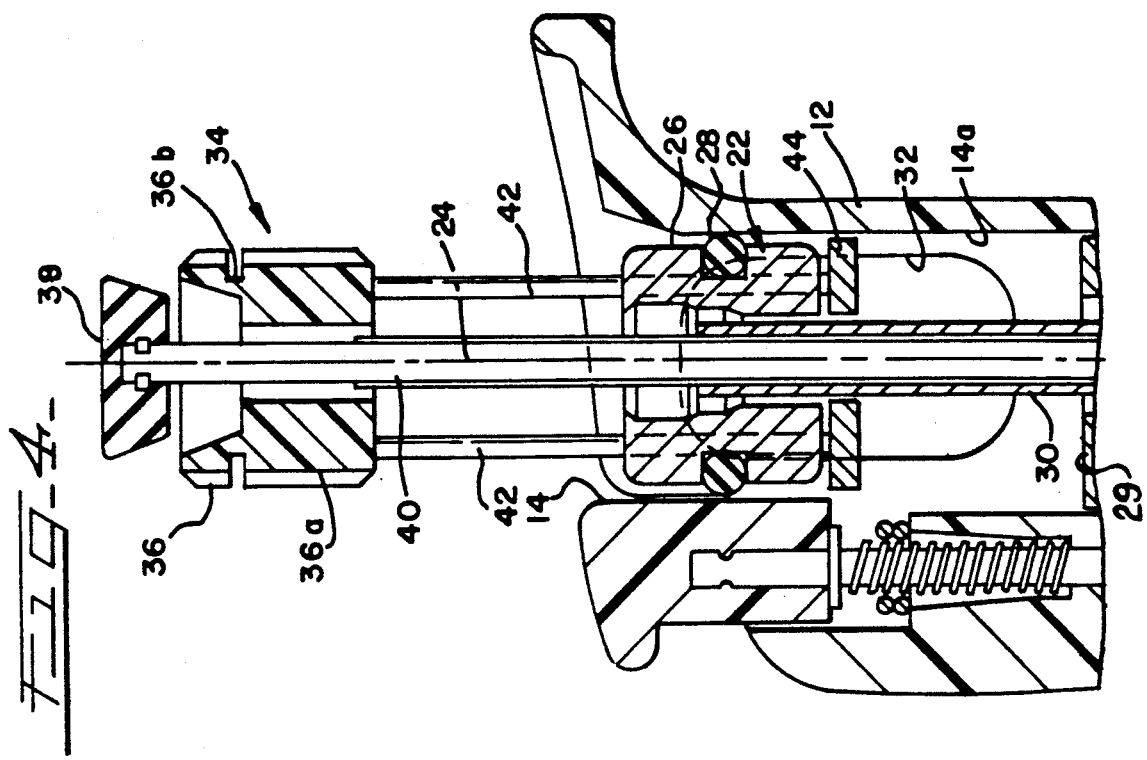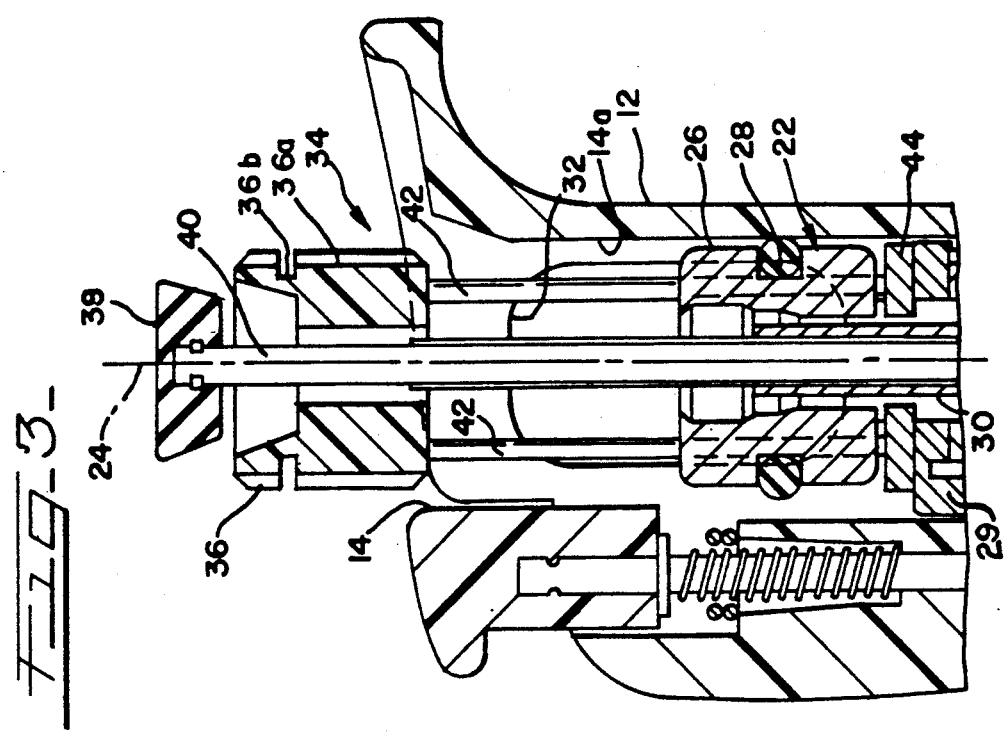

5,018,394

1

CONTINUOUSLY ADJUSTABLE DILUTING DEVICE FOR MIXING PREDETERMINED VOLUMES OF LIQUID

BACKGROUND OF THE INVENTION

1. Field of the Invention

The present invention relates to a new and improved continuously adjustable diluting device for mixing predetermined volumes of liquid. These devices are commonly called pipettes and are widely used in medical laboratory work for intermixing precise volumes of a liquid sample and a diluting medium. U.S. Pat. No. 4,141,250 discloses a plural piston adjustable diluting device having a volume indicator assembly and the present invention is an improvement over that device in providing an exceptionally handy system for selectively determining a precise volume of liquid sample or diluent to be picked up when the diluting device is utilized.

2. Background of the Prior Art

The aforementioned U.S. Pat. No. 4,141,250 discloses a plural piston adjustable diluting device having a digital volume indicator assembly which provides a digitial readout for indicating the precise volume in milliliters of a sample of liquid to be drawn into the device and thereafter expelled after mixing with a predetermined volume of liquid diluent. Oftentimes diluting devices are handled by laboratory technicians wearing rubber gloves in order to avoid contamination and sometimes when carelessly manipulating the diluting device to a precisely selected volume, a portion of a thin rubber glove may become wedged or caught within a space formed between an internal adjustment knob and an adjacent wall surface of the body of the diluting device. Moreover, fine adjustment of a volume to a precise level as indicated by digital readout is sometimes difficult to obtain with gloves on because of the limited access or area available for turning an internally positioned volume adjustment member. Moreover, because of frictional engagement between the knob and surrounding wall surface, a relatively large amount of finger strength is required to make a volume adjustment.

OBJECTS OF THE INVENTION

In view of the foregoing difficulties, it is a general object of the present invention to provide a new and improved continuously adjustable diluting device and more particularly, a continuously adjustable liquid mixing device especially adapted for intermixing selectively adjustable volumes of several liquids.

It is another object of the present invention to provide a new and improved continuously adjustable intermixing device employing a new and improved externally accessible system for selectively adjusting at least one of the liquid volumes.

More particularly, it is another object of the present invention to provide a new and improved liquid diluting device of the character described having an externally accessible, easily turnable adjusting element for rotatively driving an internal volume adjusting system of a diluting device to select a predetermined volume of liquid to be sampled or diluted.

Still another object of the present invention is to provide a new and improved adjustable diluting control for use on a device as disclosed in the aforementioned U.S. Pat. No. 4,141,250, which requires a minimal redesign of components in the patented device.

Still another object of the present invention is to provide a new and improved adjustable diluting device of the character described which is extremely simple to use and which does not require substantial finger strength in order to easily obtain a desired volume adjustment.

SUMMARY OF THE INVENTION

The foregoing objects and advantages of the present invention are accomplished in a new and improved continuously adjustable diluting device for intermixing selectively adjustable volumes of several liquids including a base or body for containing a plurality of volumes of liquids and having an open recess at an upper end. A system is provided for drawing up respective volumes of liquid into the body and thereafter expelling the liquid from a lower end. A volume adjustment mechanism is provided for adjusting the size of at least one of the liquid volumes and this element includes a rotary element mounted within the body recess and frictionally engaging a wall surface thereof for retaining a volume that is selected during an adjustment operation of the mechanism. An external drive mechanism is provided for rotatively driving the volume adjustment system in the body. The drive mechanism includes a knob adjacent an upper end of the body and movable outwardly thereof so that volume adjustment can be easily and rapidly accomplished with a minimum of finger strength and manual dexterity being required. The drive mechanism is retractable to an inward position when not in use and does not get in the way of a normal operation of the device. The external drive mechanism also readily lends itself to a power driven mechanical drive system which may be used for providing a desired adjustment in a more rapid fashion.

BRIEF DESCRIPTION OF THE DRAWINGS

For a better understanding of the present invention, reference should be had to the following detailed description taken in conjunction with the drawings, in which:

FIG. 1 is a side elevational view of a new and improved adjustable diluting device constructed in accordance with the features of the present invention;

FIG. 2 is a perspective view of an external drive mechanism for rotatively driving a volume adjustment system of the diluting device in accordance with the present invention;

FIG. 3 is a fragmentary cross-sectional view taken substantially along lines 3-3 of FIG. 1; and FIG. 4 is a similar fragmentary cross-sectional view showing the drive mechanism and components of the diluting device in a different operational position with respect to that shown in FIG. 3.

DETAILED DESCRIPTION OF A PREFERRED EMBODIMENT OF THE INVENTION

Referring now more particularly to the drawings, therein is illustrated a new and improved continuously adjustable liquid diluting device for mixing a predetermined volume of a liquid sample with a predetermined volume of a liquid diluent and constructed in accordance with the features of the present invention. The device is indicated in FIG. 1 generally by the reference numeral 10 and includes an elongated body 12 preferably formed of molded plastic material to include an axially aligned cylindrical recess 14 opening at the upper end of the body. A lower, tapered, tubular element or nose member 16 is attached to a lower end of the body by means of a fluted nut 18.

As more fully described in the aforementioned U.S. Pat. No. 4,141,250, incorporated herein by reference, the diluting device 10 includes first and second chambers in the nose member 16 adapted to hold predetermined volumes of a liquid sample and a liquid diluent which are drawn up through an opening in a lower end portion 20 of the nose member 16 during a diluting operation.

The diluting device 10 includes an internally positioned volume adjustment assembly 22 mounted for rotation in the body recess 14 for movement along a central axis of the recess indicated by the axial line 24 in FIGS. 1, 3 and 4. The volume adjustment assembly 22 includes a generally cylindrical knob-like actuator 26 formed of molded plastic and provided with an external groove at a mid-level for holding a resilient 0-ring 28 adapted to frictionally engage an inside wall surface 14a of the recess 14 to normally retain the position of the actuator after an adjustment is made.

The actuator 26 is secured to the upper end of an elongated, hollow, axially extending threaded element 30 which projects downwardly along the axis 24 into the lower end of the body 12 for adjusting the precise volume of a liquid sample that is drawn up into the diluting device 10 as more fully described in U.S. Pat. No. 4,141,250. The body 12 is provided with a pair of oblong windows 32 on opposite sides adjacent the upper end portion for exposing the actuator 26 so that manual rotation can be accomplished to provide a precise volume selection as required and as indicated in a digital readout mechanism 29, more fully described in U.S. Pat. No. 4,141,250.

When using the actuator 26 to adjust a volume of a liquid sample, sometimes a laboratory worker's glove tends to catch or become lodged in a window 32 between the edge of the actuator 26 and the adjacent surface 14a or the 0-ring 28. Moreover, sometimes it is difficult to rotate the actuator 26 a desired amount because of the limited access through the windows 32. This is especially true for people not having good finger strength or good manual dexterity In accordance with the present invention, the diluter device 10 includes a new and improved retractable, external drive mechanism 34 which is accessible exteriorly of the body 12 for rapidly adjusting the desired volume of liquid to be sampled in the diluter device. The drive mechanism 34 includes an upper, generally cylindrical, drive knob 36 preferably formed of molded plastic material and provided with a plurality of axially extending grooves or flutes 36a on the outer surface to facilitate turning of the knob manually or with a motor driven friction wheel The knob 36 also is provided with an annular groove 36b near the upper end to facilitate pulling the knob upwardly from the retracted position of FIG. 3 to an operational position as shown in FIG. 4 ready for manual rotation. The groove 36b permits a user to insert fingernails for easily pulling the knob upwardly.

The knob 36 also includes a frustoconical-shaped recess 38 in the upper, outer end face thereof in coaxial alignment with the axis 24 in order to receive a push button 39 mounted on the upper end of a central shaft 40 of the plunger mechanism of the diluter device. As described in U.S. Pat. No. 4,141,250, the shaft is displaced longitudinally when operated to withdraw and expel liquid samples into the respective volumes of the device 10.

The external adjustment knob 30 includes a central opening to accommodate the shaft 40 and is secured to the outer ends of a plurality of elongated support rods 42 arranged in parallel with the shaft and spaced equilaterally and radially outwardly thereof to form a cage-like structure as shown in FIGS. 1 and 2. The support rods 42 are slidably supported for axial sliding movement in a plurality of apertures provided in the internally positioned actuator 26 and, accordingly, the knob 36 is movable between an inward or retracted position as shown in FIG. 3 and an outward or operative position as shown in FIG. 4, ready for making easy rotary adjustments in the position of the actuator 26.

On the inner ends, the rods 42 are connected to a common annular stop ring 44 which is engageable with the lower end of the actuator 26 to limit the upward travel of the knob 36. It has been found that the new and improved external drive mechanism 34 provides a much easier system for rotatively adjusting the actuator 26 to select a desired sample volume for the diluting device 10. The drive mechanism requires only a few modifications of the structure of the original diluter device of U.S. Pat. No. 4,141,250 but yet provides an adjustment system that is much easier to operate for adjusting sample volumes.

Many modifications and variations of the present invention are possible in light of the foregoing specification and thus, it is to be understood that within the scope of the appended claims, the invention may be practiced otherwise than as specifically described.

What is claimed and desired to be secured by Letters Patent of the United States is:

1. An adjustable diluting device for mixing a predetermined volume of a liquid sample with a predetermined volume of a liquid diluent, at least one of said volumes being variable, comprising:
   a body having an elongate chamber open at an upper end of said body and extending downwardly along a central axis thereof;
   a volume adjustment mechanism for one of said volumes rotatably mounted in said chamber and including a rotating adjustment element frictionally engaging an adjacent wall surface of said chamber for retaining an adjusted position in said chamber;
   means for rotating said adjustment element supported for longitudinal movement relative thereto along said axis between a retracted position relative to said body and an outwardly extended externally exposed, operative position readily accessible adjacent said open upper end of said body for rotating said adjustment element to vary said one volume;
   the rotating means including knob means secured adjacent an outer end portion of an elongate support element slidably supported from said adjustment element for movement longitudinally of said axis between said retracted and said operative positions; and
   the elongate support element comprising at least one member slidably mounted in said adjustment element spaced radially outward and parallel of said axis.

2. The diluting device of claim 1, wherein:
   said elongated support element is positioned radially outward of said axis and parallel thereto.

3. The diluting device of claim 1, including:

means including a shaft extending along said axis and outwardly of said knob means having a push button at an outer end movable toward and away from said knob means for expelling and drawing up said volumes of liquid sample and liquid diluent.

4. The diluting device of claim 3, wherein:
said knob means includes a recess in an outer surface thereof for receiving said push button when moved toward said knob means.

5. The diluting device of claim 1, wherein:
said knob means includes a fluted outer surface for facilitating rotation thereof.

6. The diluting device of claim 1, including:
stop means secured adjacent an inner end of said elongate support element for limiting outward travel of said knob means to said operative position.

7. An adjustable diluting device for mixing a predetermined volume of a liquid sample with a predetermined volume of a liquid diluent, at least one of said volumes being variable, comprising:
a body having an elongate chamber open at an upper end of said body and extending downwardly along a central axis thereof;
a volume adjustment mechanism for one of said volumes rotatably mounted in said chamber and including a rotating adjustment element frictionally engaging an adjacent wall surface of said chamber for retaining an adjusted position in said chamber;
means for rotating said adjustment element supported for longitudinal movement relative thereto along said axis between a retracted position relative to said body and an outwardly extended externally exposed, operative position readily accessible adjacent said open upper end of said body for rotating said adjustment element to vary said one volume;
the rotating means including knob means secured adjacent an outer end portion of an elongate support element slidably supported from said adjustment element for movement longitudinally of said axis between said retracted and said operative positions;
stop means secured adjacent an inner end of said elongate support element for limiting outward travel of said knob means to said operative position; and
said elongate support element comprising at least one rod slidably mounted in said adjustment element on opposite sides of said axis in parallel therewith.

8. The diluting device of claim 7, wherein:
said knob means and said stop means comprise annular members having a central opening aligned on said axis and opposite ends of said elongate rods are secured to said knob means and said stop means radially outwardly of said central openings.

9. An adjustable diluting device for mixing a predetermined volume of a liquid sample with a predetermined volume of a liquid diluent, at least one of said volumes being variable, comprising:

a body having an elongate chamber open at an upper end of said body and extending downwardly along a central axis thereof;
a volume adjustment mechanism for at least one of said volumes rotatably mounted in said chamber and including a rotating adjustment element mounted in said body frictionally engaging an adjacent wall surface of said chamber for retaining an adjusted position in said chamber; and
means including a knob for rotating said adjustment element and supported for reciprocal longitudinal movement relative to said adjustment element along said axis between a retracted inward position wherein said knob is positioned adjacent to said upper open end of said chamber and an outwardly extended, externally exposed, operative position wherein said knob is readily accessible for rotation and is spaced from said open upper end of said body for easily rotating said adjustment element to vary said one volume.

10. The diluting device of claim 9, wherein:
said knob is secured adjacent an outer end portion of at least one elongate support element slidably supported from said adjustment element for movement longitudinally of said axis between said retracted and said operative positions.

11. The diluting device of claim 10, wherein:
said elongated support element is positioned radially outward of said axis and parallel thereto.

12. The diluting device of claim 10, including:
means including a shaft extending along said axis and outwardly of said knob having a push button at an outer end movable toward and away from said knob for expelling and drawing up said volumes of liquid sample and liquid diluent.

13. The diluting device of claim 12, wherein:
said knob includes a recess in an outer surface thereof for receiving said push button when moved toward said knob.

14. The diluting device of claim 10, wherein:
said knob includes a fluted outer surface for facilitating rotation thereof.

15. The diluting device of claim 10, wherein:
said elongate support element comprises a plurality of elongate rods slidably mounted in said adjustment element spaced radially outward and parallel of said axis.

16. The diluting device of claim 10, including:
stop means secured adjacent an inner end of said elongate support element for limiting outward travel of said knob means to said operative position.

17. The diluting device of claim 16, wherein:
said elongate support element comprises a plurality of elongate rods slidably mounted in said adjustment element on opposite sides of said axis in parallel therewith.

18. The diluting device of claim 17, wherein:
said knob and said stop means comprise annular members having a central opening aligned on said axis and opposite ends of said elongate rods are secured to said knob and said stop means radially outwardly of said central openings.

* * * * *